United States Patent [19]

Foody

[11] Patent Number: 4,461,648
[45] Date of Patent: Jul. 24, 1984

[54] METHOD FOR INCREASING THE ACCESSIBILITY OF CELLULOSE IN LIGNOCELLULOSIC MATERIALS, PARTICULARLY HARDWOODS AGRICULTURAL RESIDUES AND THE LIKE

[76] Inventor: Patrick Foody, 3870 Cote Vertu, St. Laurent, Quebec, Canada, H4R1V4

[21] Appl. No.: 269,185

[22] Filed: Jun. 1, 1981

Related U.S. Application Data

[63] Continuation-in-part of Ser. No. 168,326, Jul. 7, 1980, abandoned.

[51] Int. Cl.³ .............................................. A23K 1/12
[52] U.S. Cl. ...................................... 127/37; 162/15; 162/2.1; 162/22; 162/68; 426/807; 435/165
[58] Field of Search ...................... 162/21, 22, 68, 15, 162/16; 127/37; 435/101, 165; 426/2, 807

[56] References Cited

U.S. PATENT DOCUMENTS

| | | | |
|---|---|---|---|
| 1,979,341 | 11/1934 | Olsen | 162/21 |
| 2,459,570 | 1/1949 | McGregor | 162/16 |
| 3,183,145 | 5/1965 | Collins, Jr. | 162/15 |
| 3,212,932 | 10/1965 | Hess et al. | 127/37 |
| 3,212,933 | 1/1965 | Hess et al. | 127/37 |
| 3,523,911 | 8/1970 | Funk et al. | 127/37 |
| 3,667,961 | 6/1972 | Algeo | 426/2 |
| 3,817,786 | 6/1974 | Algeo | 127/1 |
| 3,817,824 | 6/1974 | Marks | 162/15 |
| 3,939,286 | 2/1976 | Jelks | 426/807 |
| 4,070,232 | 1/1978 | Funk | 162/16 |
| 4,136,207 | 1/1979 | Bender | 426/807 |
| 4,163,687 | 8/1979 | Mamers et al. | 162/22 |
| 4,243,686 | 1/1981 | Israilides et al. | 426/807 |

FOREIGN PATENT DOCUMENTS

| | | |
|---|---|---|
| 933028 | 9/1973 | Canada . |
| 2000822 | 1/1979 | United Kingdom ................. 162/21 |

OTHER PUBLICATIONS

Paper Trade Journal, Mar. 30, 1944, pp. 35–37, (P&J).
Energy Research Abstracts, vol. 5, No. 22, #34662, Nov. 30, 1980.
Foody, Final Report, "Optimization of Steam Explosion Pretreatment", by Iotech Corporation (D.O.E. Report ET230501, dated Apr., 1980).

Primary Examiner—William F. Smith
Attorney, Agent, or Firm—David H. Semmes; Warren E. Olsen

[57] ABSTRACT

This invention comprises a method for increasing the accessibility of cellulose in lignocellulosic materials to chemical or biochemical reagents. The material is steam cooked for a predetermined time, then rapidly depressurized. A venting sequence is used to remove volatiles from the reactor. Optimal cooking times for normal and acid catalyzed cooking are disclosed, according to the discovery of a novel set of governing equations, wherein optimum cooking times can be determined as a time integration of reactor pressure.

38 Claims, 6 Drawing Figures

METHOD FOR INCREASING THE ACCESSIBILITY OF CELLULOSE IN LIGNOCELLULOSIC MATERIALS, PARTICULARLY HARDWOODS AGRICULTURAL RESIDUES AND THE LIKE

CROSS-REFERENCE TO RELATED APPLICATIONS

This application is a continuation-in-part of my co-pending application Ser. No. 168,326, filed July 7, 1980 now abandoned.

BACKGROUND OF THE INVENTION

1. Field of the Invention

Methods for making the cellulose component in lignocellulosic materials more accessible to micro-organisms, enzymes and the like are of great interest in many practical applications. These include, for example, using the lignocellulose as animal feed or treating it with enzymes so as to produce sugar. Due to the material's complex chemical structure, however, microorganisms and enzymes can not effectively attack the cellulose without pretreatment. The cellulose is described as 'inaccessible' to the enzyme or bacteria. The effect is illustrated by the inability of cattle to digest wood.

It is the primary goal of this invention to reduce the problem of inaccessibility of cellulose within hardwoods and agricultural residues such as bagasse and straw so as to render the cellulose in such materials more accessible to attack by rumen bacteria, microorganisms, enzymes and the like. This is done using a highly critical set of operating parameters for steam cooking the material. These conditions optimize the accessibility of the cellulose. This accessibility is measured by either the in vitro cellulose digestibility to rumen bacteria or by the yield of sugar when the lignocellulose is treated by cellulase enzymes.

Lignocellulosic materials have three major components: cellulose, hemicellulose and lignin. Cellulose is a linear polysaccharide built up to gluco-glycosidic bonds. It has a relatively well-ordered structure, is pseudo-crystalline, and has a high enough chain length to be insoluble in water or dilute acids and alkali at room temperature. Cellulose is the major structural component of the cell wall and can be isolated as fibre.

Hemicelluloses are non-cellulosic polysaccharides. They are built up mainly of sugars other than glucose, are generally poorly ordered and non-crystalline, and have a much lower chain length than cellulose. The hemicelluloses occur in intimate association with the cellulose in certain layers of the cell wall, as well as in close association with the lignin between cells.

Lignin is an aromatic polymer, phenolic in nature, and built up from phenylpropane units. It has no systematic structure. Lignin occurs mainly as an encrusting agent between the fibres and on the outer layers of the cell wall.

The cellulose in lignocellulosic material is poorly accessible to micro-organisms, to enzymes and the like. That is, the micro-organisms can not easily react with the cellulose. This is due to its close association with lignin and hemicellulose in the cell structure, and to its highly cross-linked and crystalline molecular structure. To improve the accessibility, one must rupture the cell and break the close association with lignin.

2. Brief Description of the Prior Art

It has been known for some time that steam cooking changes the properties of lignocellulosic materials. The original and most broadly reported work on steam cooking with respect to such materials as hardwoods was carried out by Mason and is reflected in his various U.S. Pat. Nos. 1,824,221; 2,645,633; 2,494,545; 2,379,899; 2,379,890; 2,759,856. Mason's processes generally involved an initial slow cooking at low temperatures to glassify the lignin. This was followed by a very rapid pressure rise and quick release. The pressurized material blown from his reactor through a die caused defibration of the wood and resulted in the "fluffy", fibrous material commonly used in the manufacture of "Masonite" boards.

While Mason's work was directed towards the preservation of fibre for board production, some of the more recent research in steam cooking has centered on breaking down the fibre structure so as to increase the material's rumen digestibility. This work reflects a desire to increase the cellulose accessibility and therefore shares the goal of the present invention. Contributions have been made by Algeo, Bender, Delong, and Jelks and will be outlined below. First, however, a general note about steam cooking is in order.

In any steam cooking procedure, there are certain well known facts. The pressure of saturated steam in a reactor vessel, for example, has a well-defined relationship with temperature. It is also well understood that an inverse relationship exists between cooking time and temperature. Thus, when a pressure range is stated in conjunction with a range of cooking times, the shorter times are associated with the higher pressures, and the longer times with the lower pressures.

Algeo (U.S. Pat. No. 3,667,961) describes work upon ligno-cellulosic materials such as straw and almond hulls to produce feeds with cooking carried out at relatively high pressures. Algeo used steam cooking and explosive release with equipment physically similar to Mason's, adjusting cooking times so as to cause a greater breakdown of the lignocellulosic bonds. The material produced had a fine "sponge-like" texture.

Algeo also tested a variety of non-lignocellulosic materials (almond shells, coffee grounds) and found pressures and cooking time ranges to be "very critical for each commodity" (Col. 11, line 56). He noted that from a digestibility perspective, catalyzing the hydrolysis reaction drastically over-processes the material and can cause undesireable sugar production. That is, he found that converting the cellulose to sugar was unnecessary and, in fact, harmful when the goal was to produce cattle feed. His process was therefore carried out without the addition of catalysts. Table 1 lists Algeo's obviously preferred range for straw, a lignocellulose equivalent in structure to the hardwood and bagasse materials taught as preferred herein, based upon a understanding of his Table F, col. 11 as requiring the shorter times for the higher pressures.

TABLE 1

| Pressure | Time |
|---|---|
| 400 psig | 90 sec. |
| 500 psig | 60 sec. |

Jelks (U.S. Pat. No. 3,933,286) proposed a two-stage process for the production of animal feed which first involved oxidation in the presence of a metal catalyst, then hydrolysis with an acid catalyst. Both reactions were at low pressures with moderate cooking times. He found the oxidation served to break a portion of the "lignin-cellulose bonds" and to fragment some cellulose molecules. The hydrolyzation then converted a portion of the cellulose made accessible in oxidation to saccharides and saccharide acids. He notes the oxidation step prior to hydrolyzation substantially increased sacchrification. Jelks' work is an extension of the earlier hydrolysis efforts criticized by Algeo. Rather than simply increasing accessibility, these workers carried out a full hydrolysis to sugar. Jelks' major contribution was in illustrating the beneficial effects of metal catalyzed oxidation in aiding hydrolysis. Table 2 lists his conditions.

TABLE 2

|  | Temperature | Pressure | Time |
|---|---|---|---|
| Oxidation | 105–110° C. | 150 psi | 15–20 mins. |
| Hydrolyzation | 180° C. | 135–150 psi | 3–7 mins. |

Bender (U.S. Pat. No. 4,136,207) described a low pressure, long residence time steam cooking process using a continuous plug-feed, plug-release reactor. He cited the economic benefits of lower pressure, which allow lighter equipment, but nevertheless noted that steam cooking can be applied through the full range of pressures. He also found that the use of chemical reagents was unnecessary. Table 3 lists his preferred times for aspen wood, a material very similar to straw, again based upon an understanding of his broad claim 8 that the shorter times are to be associated with the higher pressures.

TABLE 3

| Pressure | Time |
|---|---|
| 210 | 1200 sec. |
| 250 psig | 300 sec. |

Bender cautioned that cooking longer than this could lead to overcooking and consequent reductions in yield. It is interesting to note Bender teaches that oxidation, which Jelks found to aid hydrolysis, will actually decrease the yield of digestive material, thereby illustrating the basic disagreements in the prior art of this general technology.

More recently, Delong (British Application No. 2941.7/78, filed July 11, 1978 and published Jan. 17, 1979 as G.B. No. 2,000,822A) has proposed a Mason-type steam explosion process for fracturing the linkages between lignin, hemicellulose, and cellulose for the exact preferred food materials addressed herein, aspen wood chips, allegedly to make the cellulose and hemicellulose more readily accessible to both rumen microflora and enzymes. His material has the appearance of "potting soil" and "sinks like a stone in water".

Delong proposed a largely physical explanation for improved accessibility, i.e., since cellulose softens at a temperature of 230° C., when wood is exploded in such a softened state, the fibre structure will simply be destroyed, thereby opening the cellulose and hemicellulose to attack.

Delong found that cooking at or above this 230° C. temperature would only serve to promote an undesirable hydrolysis of the hemicellulose. Delong maintained that Algeo had substantially overcooked his material, causing a "drastic reduction in the fermentation value of the hemicellulose". Delong's stated objective was to make the cellulose highly accessible while minimizing this hemicellulose hydrolysis, and allegedly this was to be done by raising the temperature as rapidly as possible to the critical softening point, then immediately exploding the material.

Delong experimentally inferred that the best yields were obtained when the mass temperature (as measured by an unspecified probe projecting into the mass of chips) reached 238° C. This was accomplished by adding 650 psi steam (258.4° C. saturation temperature) to the reactor. In contrast, Bender noted (and this inventor's work can confirm), that such probe temperatures actually reflect only the saturated steam temperature in the reactor, and in Bender's continuous process no thermal probe response time characteristics were present. Thus, whereas previous workers had proposed steady-state cooking, Delong suggested exploding before reaching steady-state. The present invention clearly avoids such thermal measurement inaccuracies by adopting a more straightforward technique, sensing only reactor saturated steam pressure.

Algeo and Bender share a common goal with the present inventor, and certain similarities in the present inventor's basic approach, i.e., both Algeo and Bender seek to render the cellulose component of wood more accessible so that the output material can be used for future treatment, such as by enzymes or rumen bacteria. Hence, Algeo and Bender are relevant prior art, in that they are concerned with the treatment of natural wood, to increase the accessibility of the cellulose. While Delong also professed this same goal, Delong categorically took an approach which was to avoid any steady-state temperature circumstances, since Delong specifically sought to avoid any thermally-induced hydrolysis. (See Delong at page 3, lines 10+). Delong, which is the most recent of these three pertinent references, essentially taught away from inducing a thermal hydrolysis, and certainly did not teach how a specific reaction could be ensured by a cooking time that is a repeatable function of reactor pressure. Hence, the most relevant prior art appears to be the earlier teachings of Algeo and Bender, even though it is only the present invention which critically recognizes how a steady-state, thermally-induced partial hydrolysis mechanism can result in the optimization of cellulose accessibility, as most conveniently measured by the yield of glucose when the material is treated with a commercial cellulase enzyme under carefully controlled conditions. In order to prove the present invention, there follows various examples and graphic representations of how glucose yield increases to a surprising optimum, and how a sharp parameterization of the discovered mechanism was derived, to explain the surprising results.

Unlike the mutual goals of Delong, Bender, Algeo and the present invention, certain prior workers were not seeking to increase cellulose accessibility, but, rather, the distinct and separate goal of directly breaking down hemicellulose to produce xylose, and cellulose to produce glucose. In other words, the present invention categorically focuses on a "pre-treatment goal" wherein a range of reaction parameters are identified so that the *cellulose* becomes most accessible for any form of subsequent treatment. Exemplary subsequent treatments include using enzymes to break down the pretreated cellulose into glucose, or simply using the pretreated material in a direct manner as feed for animals, wherein the subsequent breakdown occurs in vivo, by the bacteria in the animal's stomach.

Hess et al. (U.S. Pat. No. 3,212,932) is typical of certain non-relevant prior art teachings which seek to produce glucose directly, and through the mechanism of using a relatively high concentration of mineral acid, to brutally break down all elements of the wood feedstock. By contrast (and as also noted by Delong at page 2, lines 16–22), the present invention avoids such harsh, acid hydrolysis, since the present invention teaches that it is far preferable to hydrolyze the relatively accessible hemicellulose only, and to a point where the hemicellulose degradation products do not, in turn, adversely affect the accessibility of the cellulose. Hess et al. employ a two-stage acid hydrolysis, the first stage to recover hemicellulose-derived xylose, the second to recover cellulose-derived glucose. In the first stage, finely-divided wood in the form of sawdust or wood shavings is mixed in a ratio of 1:1 to 1:3 with a treating liquor having sulphuric acid concentration of less than 0.3% and preferably zero. This "soup" mixture is then cooked, preferably at the conditions given in Table 4.

TABLE 4

| Pressure | Time |
| --- | --- |
| 250 psig | 600 sec. |
| 600 psig | 18 sec. |

When this first cooking step of Hess et al. was complete, the pressure was rapidly reduced through a "flash blowdown". This, Hess et al. allege, served to stop the hydrolytic reaction and minimize the production of lignin degradation products, and to flash off acetic acid and other organic volatiles formed in the reaction. Delong confirmed this effect for the explosion from his Mason-type reactor.

Figure 2:
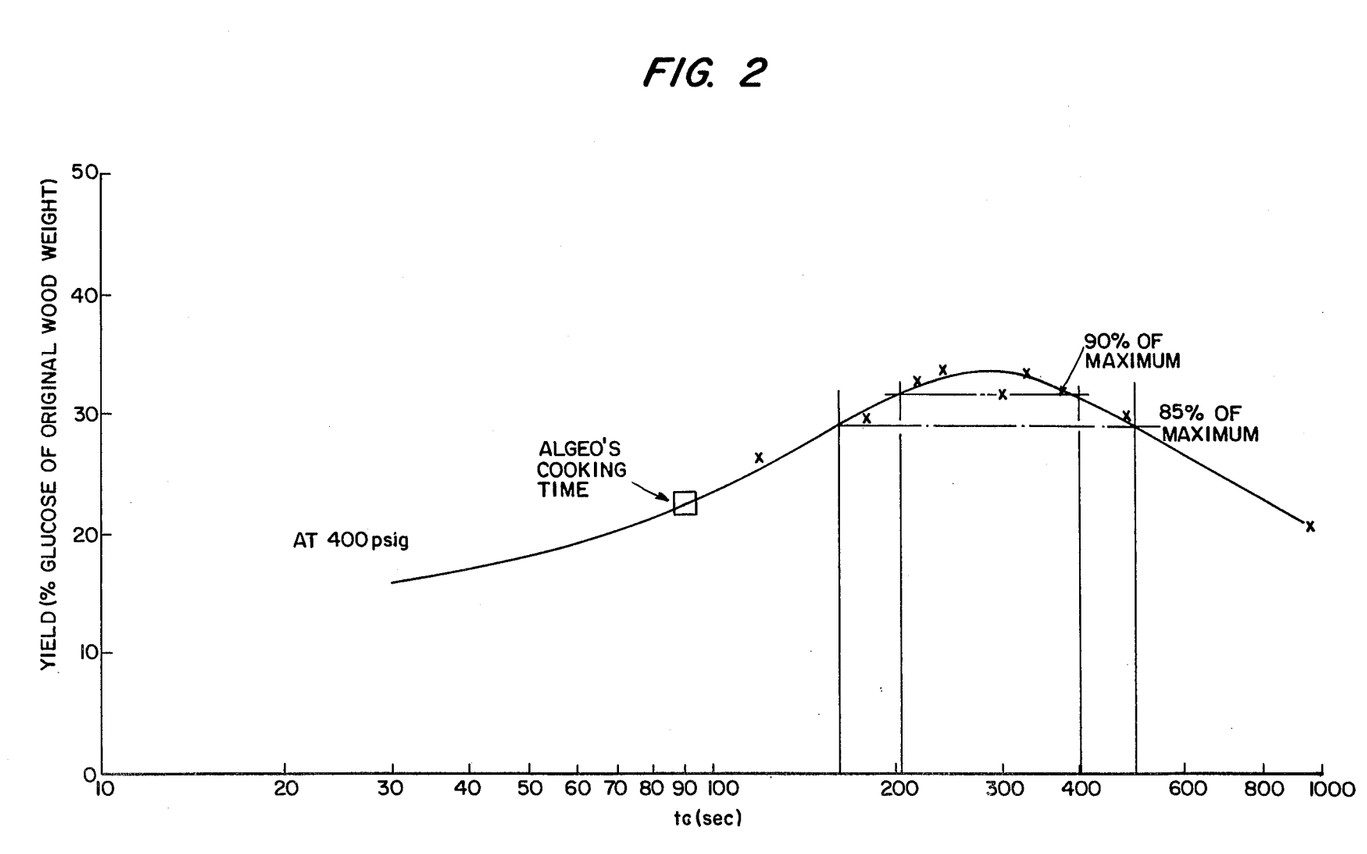
FIG. 2 is a semi-logarithmic graph of a 400 psig glucose yield (% glucose of original wood, by weight) as a function of cooking time.
Figure 3:
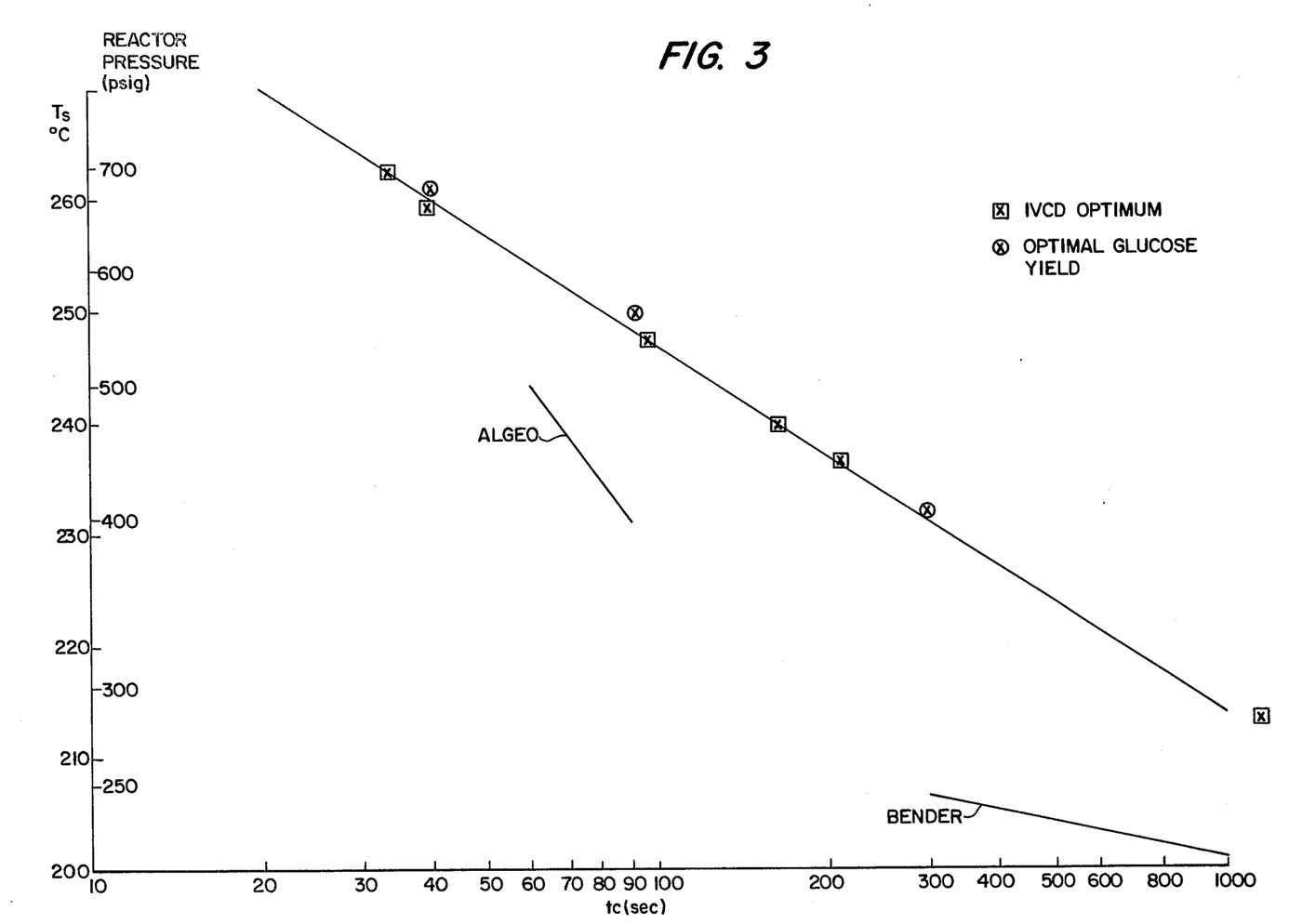
FIG. 3 is a semi-logarithmic graph of optimal cellulose accessibility reactor pressures as a function of cooking time.

By contrast, the present invention is, firstly, not performed in a "soup", but as dry chips surrounded by a steam envelope; and, secondly, Hess' pressure time parameters are not in theeenvelope shown for the present invention at FIGS. 2, 3.

Hess et al. then taught further treating the residue (from Table 4) with a 0.5% solution of sulphuric acid to remove the sugars produced. The solids are then mixed with a second treating liquor having a 0.3–3% acid concentration and cooked under the more severe conditions listed in Table 5.

TABLE 5

| Pressure | Time |
| --- | --- |
| 400 psig | 600 sec. |
| 800 psig | 18 sec. |

The second stage hydrolysis serves to convert the remaining cellulose to glucose.

Figure 1:
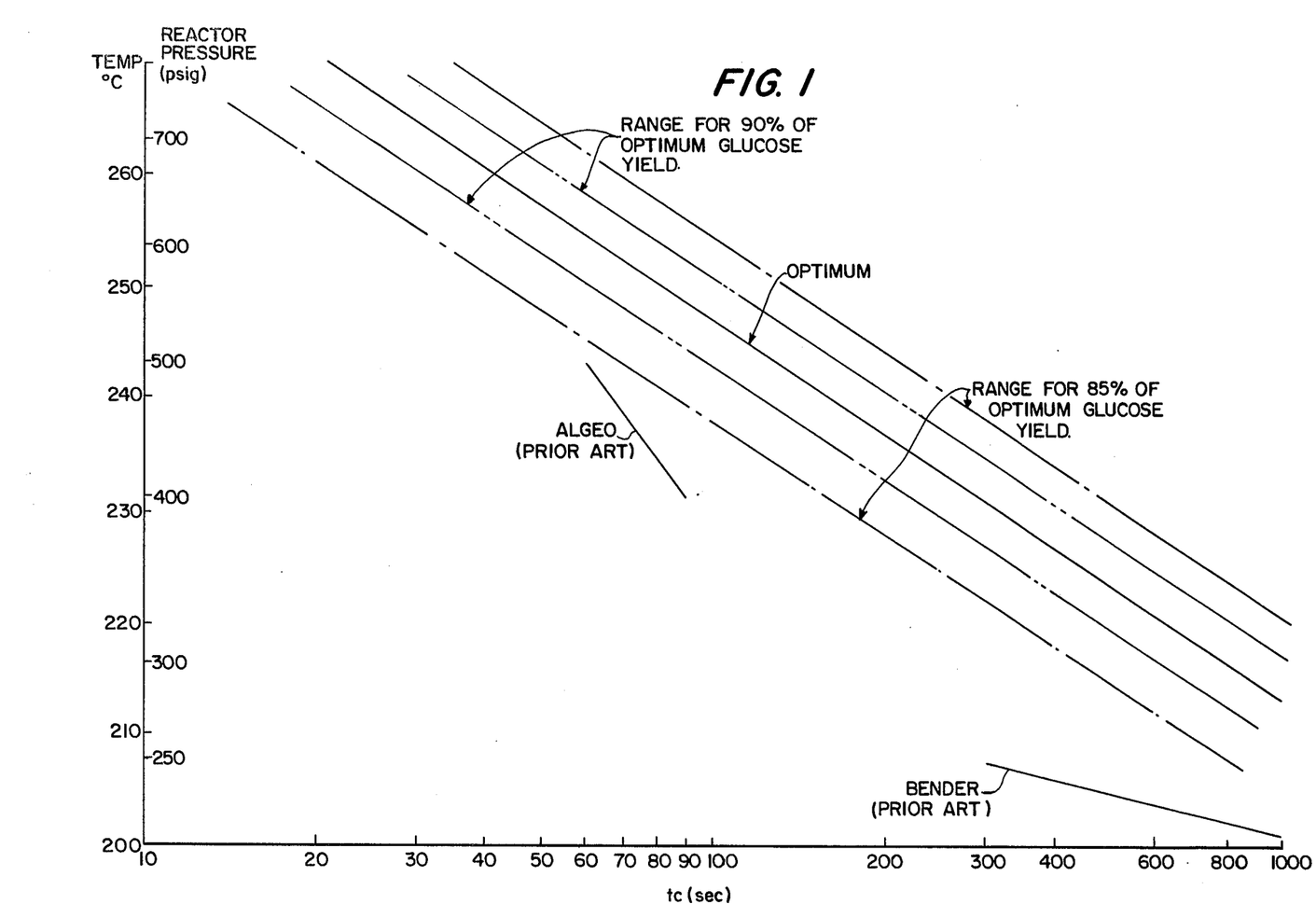
FIG. 1 is a semi-logarithmic graph of preferred reactor pressures (psig) as a function of cooking time (sec.) according to the present invention, together with the ranges taught by two prior art references.

Thus, while the present invention shares with Algeo, Bender, and Delong the ultimate goal of increasing the accessibility of cellulose to rumen bacteria (or enzymes), Hess et al. had the entirely different goal of maximizing the hydrolysis yield of glucose and xylose. FIG. 1 shows the preferred cooking times of Algeo and Bender. Delong, on the other hand, believed that accessibility was a physical result of rapid decompression. Delong proposed transient heating followed immediately by steam explosion, so as to minimize hydrolysis, and as such would correspond to a "0" steady-state cooking time, is also shown on FIG. 1.

SUMMARY OF THE INVENTION

An understanding of the mechanisms involved in steam cooking should be central in efforts to improve the basic process. There is clearly no broad agreement on these mechanisms within the prior art. The inventor has therefore developed his own description of the process. It is understood, however, that the present invention is not limited to the mechanisms postulated below.

As steam treatment begins, the hemicelluloses are hydrolyzed into relatively large intermediate oligosaccharides. Acetyl groups on the hemicellulose are also hydrolyzed to acetic acid. This acid serves to catalyze further hydrolysis. As the oligosaccharides are formed, subsequent reactions convert them into a range of degradation products. This can be symbolized by the diagram where A is the original cellulose and B the intermediate oligosaccharides. The k1 reaction effectively removes the hemicellulose from the cell structure. This removal, in concert with defibration (e.g., by explosion or refining) improves cellulose accessibility. C represents the primary degradation products such as furfural. The k2 oligosaccharide degradation to C reduces potential yields of oligosaccharide-derived pentose sugars. In the k3 reaction, the furfural appears to condense on the reactive sites of the lignin. The modified lignin adheres to the cellulose in the form of a "cap" or membrane, represented by D. This capping effect causes a sharp drop in cellulose accessibility. k1, k2, and k3 are the reaction rates of each step. During these reactions, the cellulose remains relatively unaffected. Much longer times or more severe conditions are needed for any substantial cellulose hydrolysis.

FIG. 2 shows how cellulose accessibility, as measured by the material's glucose yield in enzymatic hydrolysis, varies with cooking time. There is an initial rise as hemicellulose is converted to oligosaccharides, then a peak and drop as the capping effect begins to predominate. Tests of glucose yield and in vitro cellulose digestibility (IVCD), a measure of cellulose digestibility to remen bacteria, were carried out on material cooked at a number of different pressures. FIG. 3 shows how the optimal cooking time varies with pressure and with Ts, the temperature of saturated steam at the reactor pressure. Note that Ts is not the "cooking" temperature (which is determined by the steam partial pressure). Nonetheless, it provides an extremely good fit with the data and is convenient experimentally, pressure being the most easily and unambiguously measured property. The optimal cooking time (sec.), when Ts (° C.) is a constant value over time, is given as follows:

$$tc = 81 \times 2^{(\frac{250-Ts}{10})} \qquad (1)$$

The data points for the time range over which one can get 85% of the optimal glucose yield (as shown in FIG. 1) are plotted at FIG. 2, and can be expressed, as follows:

$$43 \times 2^{(\frac{250-Ts}{10})} \leq tc \leq 135 \times 2^{(\frac{250-Ts}{10})} \qquad (2)$$

and a most preferred, approximately 90% optimal glucose yield, can be expressed, as follows:

$$58 \times 2^{(\frac{250-T_s}{10})} \leq tc \leq 115 \times 2^{(\frac{250-T_s}{10})} \quad (3)$$

These data points—and expressions (1), (2) and (3)—exhibit a slope (as plotted in FIG. 3), which correctly follows the slope expectable from the known fact that the rate of carbohydrate hydrolysis should be double for every 10° C.

Both FIGS. 1 and 3 graphically show how the time/pressure parameters taught by the present invention depart from the ranges taught by Algeo and Bender.

A second aspect of this invention resulted from further testing done to try to reduce the "capping" effect represented by D in the reaction kinetics. The postulated reaction mechanism indicates this would be beneficial. As noted hereinabove, Hess (and Delong) taught that the formation of lignin degradation products could be minimized simply by an atmospheric decompression (or flash blowdown). However, this inventor has found that if furfural and other volatiles are *vented* just prior to the atmospheric decompression, there will be a better than 30% improvement in animal feed efficiencies over the non-purge teachings suggested by Hess et al. in the opinion of the present inventor, a simple "flash blowdown", according to Hess, in the presence of the necessarily produced reaction volatiles, actually will aid the production of lignocellulosic degradation products. The present invention teaches an unexpected result if one removes such volatiles by purging just before a flash blowdown of the reactor, since it has been discovered that the level of resulting degradation products is thereby substantially decreased, i.e., animal feed efficiency tests show an approximate 34% increase when the volatiles are so purged, over the tests in which volatiles are not purged (see Table 6, hereinafter).

A third aspect of the present invention arises from this inventor's realization that it would also be advantageous to accelerate the pace of hemicellulose hydrolysis relative to degradation steps k2 and k3. This was realized to have two possible benefits. Firstly, cellulose accessibilities might be improved, due to the smaller relative rate of capping. Secondly, oligosaccharide degradation might be limited, while still maintaining high cellulose accessibilities. The present inventor found that such an acceleration could be effected by supplementing the natural acids in the wood, according to an unexpected parametrization with cooking time (tc).

Figure 4:
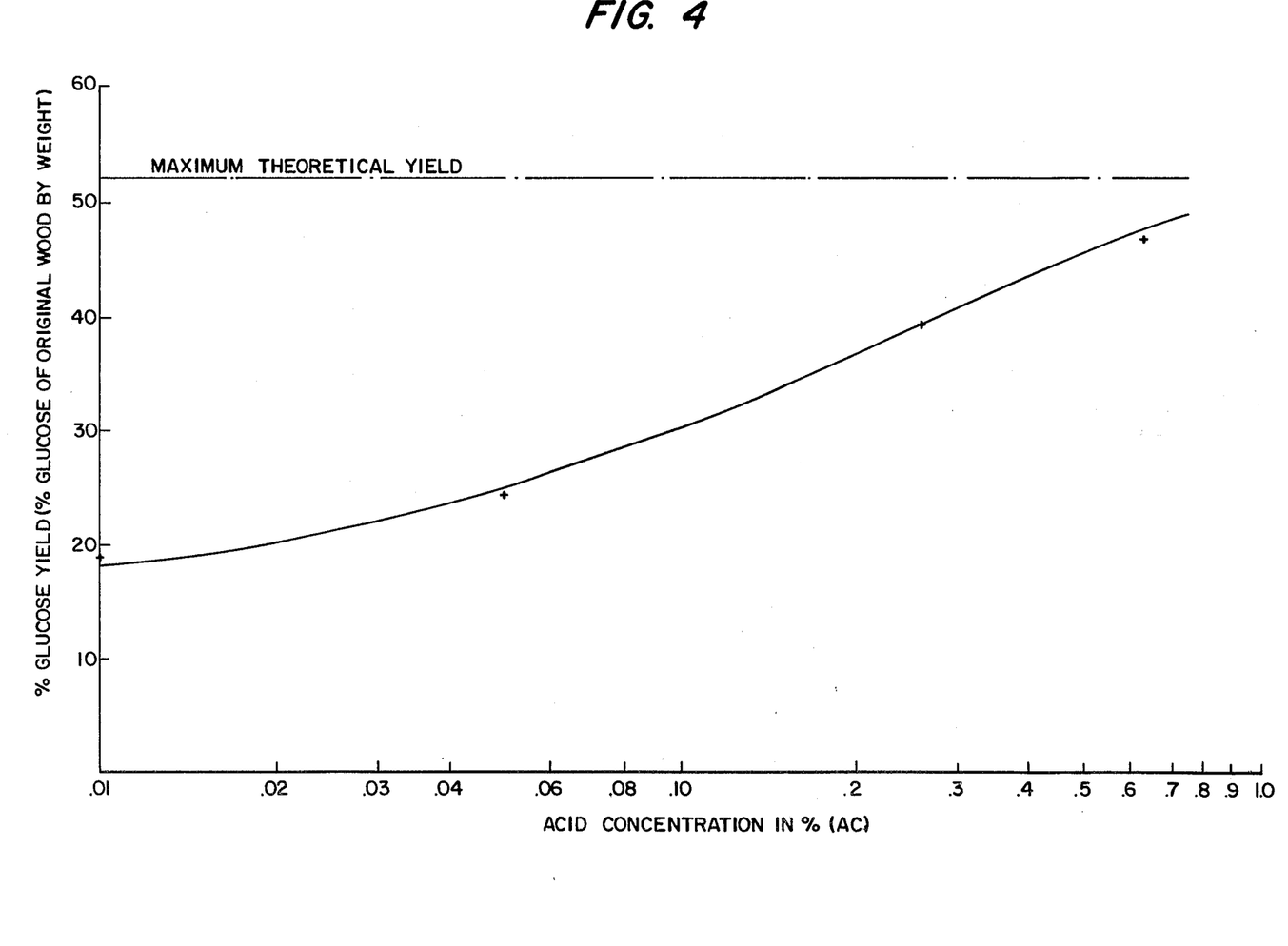
FIG. 4 is a semi-logarithmic graph of a 670 psig glucose yield as a function of acid concentration (AC)

FIG. 4 shows the effect of adding an acid catalyst on optimal glucose yields. It clearly offers massive improvements, and it is believed that the reasons for the startlingly higher accessibilites are two-fold. First, there is the catalytic effect on hemicellulose hydrolysis. Second, the acid appears to reduce the degree of polymerization of the cellulose.

Optimal cooking times were found to be governed quite well by the expression, as follows:

$$tc = \frac{81}{(1 + 80AC)^{.5}} \times 2^{(\frac{250-T_s}{10})} \quad (4)$$

where AC is the equivalent concentration of sulphuric acid which remains within the lignocellulosic feedstock fibers as a percent by weight of the lignocellulose, as measured by a titration upon the chip material after an acid exposure. When cooking times are kept below $$tc \leq \frac{135}{(1 + 2AC)^{.5}} \times 2^{(\frac{250-T_s}{10})} \quad (5)$$

yields remain relatively high and cellulose hydrolysis is kept to a minimum. Substantial hydrolysis of the cellulose indicates a high degree of overprocessing from an accessibility perspective. Note that a constant factor, R, could be chosen between 2 and 80, and substituted for the multiplicand of AC in expressions (4) and (5), and still illustrate the acid effect.

PREFERRED EMBODIMENT OF THE INVENTION

On the basis of the above discoveries, this inventor has developed three specific improvements in the steam cooking of lignocellulosic materials. In the first aspect, a well defined formula is used to specify the optimal cooking time for maximum cellulose accessibility. The second improvement involves the venting of volatiles prior to atmospheric decompression. The third improvement deals with the addition of acid catalysts to increase yields.

In the preferred embodiment of the invention, the lignocellulosic raw material should be prepared in such a way as to permit ease of handling in conveyors, hoppers and the like. In the case of wood, the chips obtained from commercial chippers are suitable, and in the case of straw it is desirable to chop the stalks into uniform pieces 2-3 inches in length.

Figure 5:
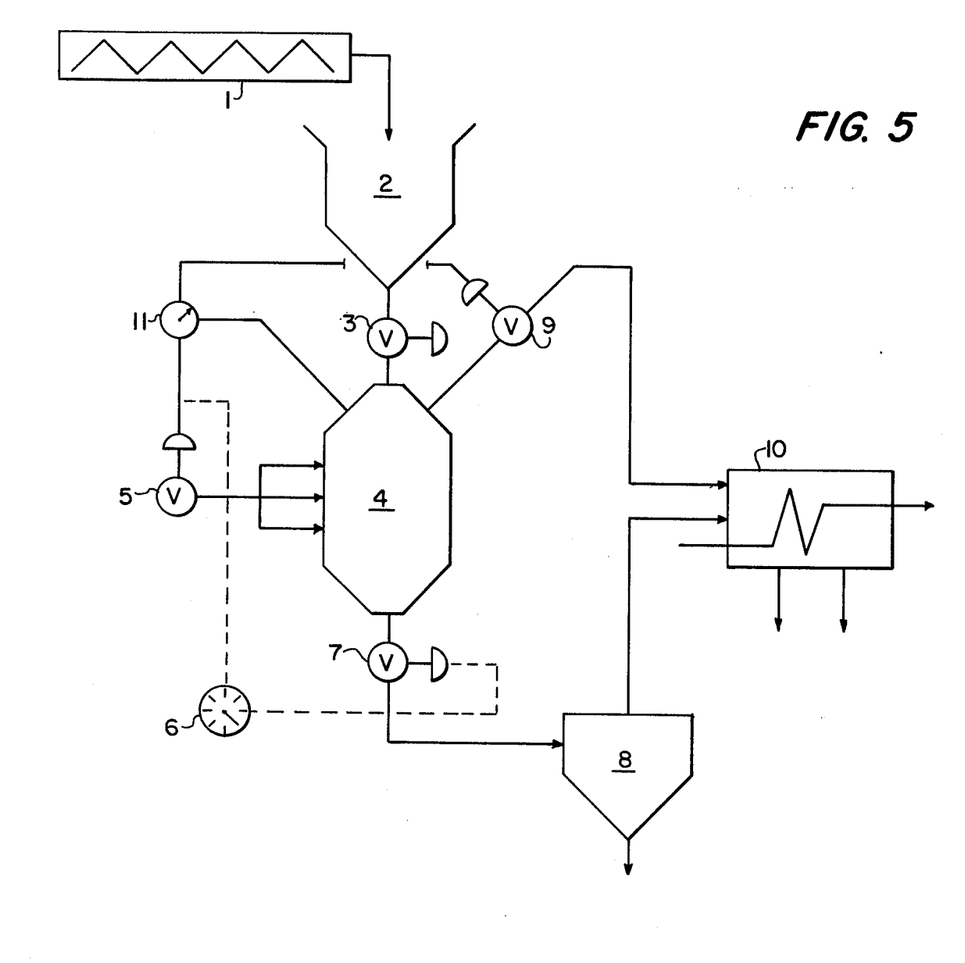
FIG. 5 is a schematic of an apparatus for practice of the present invention.

A schematic diagram of typical process equipment usable to practice the present invention is shown in FIG. 5 and is, for example, equivalent to the apparatus illustrated by the Great Britain patent to Delong, incorporated herein by reference for this purpose.

Under the first aspect of this invention, material is fed into the feed hooper, 2, by means of a screw conveyor, 1, or other device and then loaded into reactor vessel, 4, through entry valve, 3. When the reactor is full, entry valve, 3, is closed and high pressure steam is injected directly into the reactor through steam valve, 5, and distributed to several entry ports to ensure uniform penetration of the steam throughout the raw material. The reactor is filled with steam as quickly as possible, preferably within 15 seconds, to raise the vessel to the preferred operating pressure. When the operating pressure is reached on the pressure indicator controller, 11, the cooking period timer, 6, is actuated. Steam valve, 5, automatically controls the pressure at the pre-set value during the cooking period. When the selected cooking period has elapsed, discharge valve, 7, is opened and the material explosively ejected into cyclone, 8. The duration of the cooking, tc, is selected with tc, in accordance with Eq. (2): between $$43 \times 2^{(\frac{250-T_s}{10})} \leq t_c \leq 135 \times 2^{(\frac{250-T_s}{10})} \quad (2)$$

The temperature Ts is equivalent to the temperature of saturated steam at the pressure indicated by gauge, 11. Hence, at FIG. 3 the ordinate value, reactor pressure (psig) was used to derive Ts (° C.), without concern for what partial pressures were inherently present from air or wood component volatilizations. If the reactor is pressurized in a different manner than described above, for example, by the addition of an involatile gas, then Ts must be adjusted to reflect the equivalent cooking conditions, if the above method had been used.

If the reactor pressure is not held steady for the bulk of the cooking, a cooking time, $t_c$, is chosen to be within the range $t_1 \leq t_c \leq t_2$ and where $t_1$ is defined, for an 85% of optimal glucose yield, by $$\int_0^{t_1} 2^{(\frac{T_s-250}{10})} dt = 43 \quad (6)$$

and $t_2$ by $$\int_0^{t_2} 2\left(\frac{T_s-250}{10}\right) dt = 135 \quad (7)$$

where $T_s$ is the varying temperature of saturated steam corresponding to those varying reactor pressures, and is a given function of time, t.

Similarly, the more preferred embodiment range is to seek approximately a 90% of optimal glucose yield, wherein $t_1 < t_3 \leq t_c \leq t_4 < t_2$, and equation (6) shall integrate to a value of 58, and equation (7) shall integrate to a value of 115. Equations (6) and (7) simply are time integrations based directly on eq. (2), and require that the Ts variation, as a function of time, be given.

Figure 6:
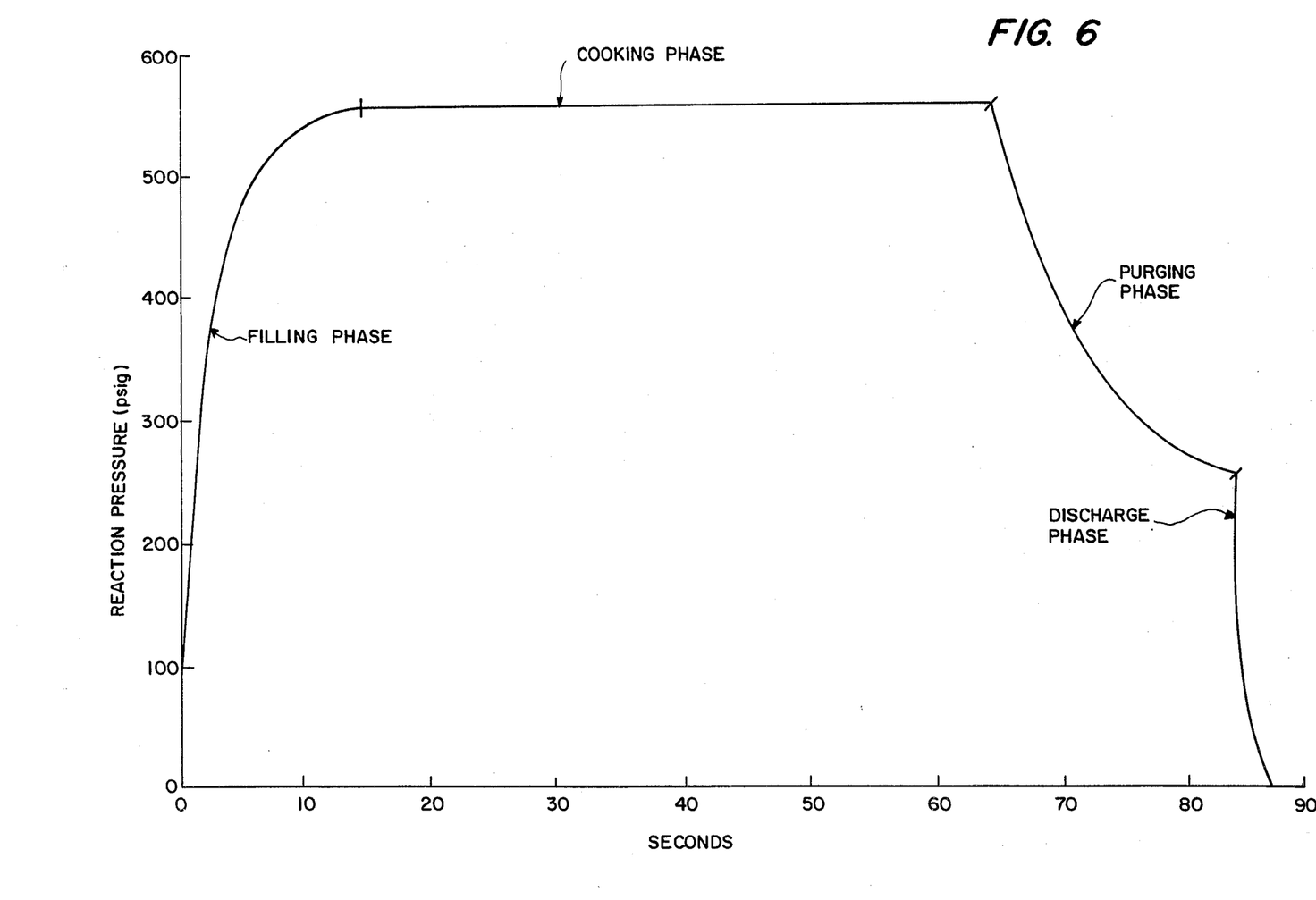
FIG. 6 is an exemplary reactor pressure variation of cooking time.

In the second aspect of the invention, the product is fed to the reactor exactly in accordance with the first aspect, but after a predetermined time, the volatile vapors are purged from the reactor by opening valve, 9. This purging sequence should be operated in such a manner that the reactor pressure is allowed to fall by at least 100 psig in a time of 10-15 seconds. When the pre-selected reduced pressure is reached, valve, 9, is quickly closed and valve, 7, opened. The material is then discharged into cyclone, 8. Cooking time are determined according to eq. (5). The purged vapors are meanwhile condensed in condensor, 10. A typical illustration of the pressure profile used for the purging aspect of the invention is shown in FIG. 6.

The present inventor found that because of the azeotrope formed between water, furfural and the miscellaneous volatile products, the steam cannot be recovered and returned to the reactor, in complete distinction to the allegations of a possible "recycle", as taught by Bender.

Under the third aspect of the invention, the natural acids in the wood are supplemented by the addition of small quantities of mineral acids, e.g., sulphuric acid. These acids may be applied to the substrate in any convenient manner. The net acid absorption into the material should preferably be between 0.1 and 1.0% by weight of lignocellulose. The lignocellulosic material is then cooked as per the preferred embodiment in the first aspect, except that the cooking time is determined by eq. (5).

$$t_c \leq \frac{135}{(1 + 2AC)^{.5}} \times 2^{(\frac{250-T_s}{10})} \quad (5)$$

or, if the reactor pressure is not held steady for the bulk of the cooking, by $t_c \leq t_2$ where $t_2$ is defined implicitly by $$\int_0^{t_2} (1 + 2AC)^{.5} 2^{(\frac{T_s-250}{10})} dt = 135 \quad (8)$$

This equation is simply a time integration based directly on eq. (5), and similarly assumes the Ts variation in time is monitored.

The process of the invention may also be carried out in continuous or semi-continuous fashion. The important element in this invention is the cooking time relation, not the feed or exit techniques.

EXAMPLE 1

First Aspect: Detailed Definition of Cooking Times and Extension of Treatment Limits Thirteen pounds (oven-dry basis) of aspen chips were loaded directly into a 1.2 cu. ft. experimental reactor. The reactor vessel was sealed and saturated steam-injected directly to fill the reactor and raise it to a predetermined operating pressure.

A fill-up period of approximately 15 seconds was required to reach the operating pressure.

When the operating pressure was reached, the cooking period timer was actuated. During the cooking period, the pressure was controlled automatically at the desired pressure by the steam injection valve.

The chips were cooked for a pre-set cooking period at various fixed pressure conditions, and at the end of that time an automatic sequence closed the steam injection valve and opened the discharge valve. The contents were instantaneously and explosively decompressed to atmospheric pressure, and ejected into a cyclone separator where the vapors present were separated. The exploded wood was collected into a hopper, weighed and bagged. Samples were taken for subsequent processing and assay. This was repeated across a broad range of pressures—taking an average of 10 shots per pressure range.

Five grams (oven-dry) of the exploded wood was combined with 9 International Units of cellulose enzyme and an equal quantity of cellobiase enzyme. The enzyme preparations used were Celluclast 100L and Cellobiase 250L. The mixture was made up to 100 g with acetate buffer and placed on a rotary shaker for 24 hours in a room maintained at a temperature of 50° C.

The hydrolyzate was sampled and assayed for glucose and zylose sugars using a High Pressure Liquid Chromatograph. Sugar results were expressed as a percentage of the oven-dry original wood loaded into the reactor.

Samples were also tested for in vitro cellulose digestibility using standard procedures and rumen microflora obtained from a control-fed fistulated cow.

The results of the tests at each pressure were plotted for IVCD and glucose yield. FIG. 2 shows the data from the 400 psig tests, and the data points which correspond to the optimal time for each reactor pressure are plotted in FIG. 3. FIG. 1 is derived from FIGS. 2 and 3, and shows 85% of optimum acceptability, as particularized by Equation (2), and the preferred 90% of optimization range, as particularized by Equation (3).

EXAMPLE 2

Second Aspect: Condensation of Volatiles

Sufficient quantity of exploded wood to feed five lambs for a period of 70 days was prepared using a method exactly equivalent to that outlined in Example 1 for the 560 psig operating pressure. A similar test was carried out for comparison purposes incorporating a purging and condensation cycle in accordance with FIG. 6. The cooking time in this case was determined using Equation (1).

The exploded wood was combined in each case into a complete ration consisting of wood, hay, barley, soybean meal, molasses, minerals and urea. The ration was formulated so that exploded wood constituted 50% of the total ration (dry matter basis), and was fed to the lambs on a free-feeding regime. The weight of the lambs was measured before and after the trial and the quantity of feed consumed was also monitored. Feeding trials were conducted using both purged and unpurged process material. Results of the feeding trial are shown in Table 6.

The ration from which the volatiles had been drawn off and condensed resulted in a higher weight gain for the lambs. The feed efficiency was also significantly better.

TABLE 6

|  | Trial 1 (Unpurged) | Trial 2 (Purged) |
|---|---|---|
| Number of lambs | 5 | 5 |
| Initial wt. (kg.) | 34.7 | 40.6 |
| Final wt. (kg.) | 40.7 | 51.7 |
| Total wt. gain (kg.) | 6.0 | 11.1 |
| Average daily gain (g.) | 142 | 264 |
| Intake as % body wt. (%) | 3.8 | 4.4 |
| lb. feed/lb. gain | 10.2 | 7.6 |

These results indicate that the accessibility of the purged steam-cooked wood is higher than that of unpurged steam-cooked wood and, as noted hereinbefore, an approximate 34% increase in feed efficiency resulted. Preliminary tests on the lignin reactivity were also carried out, and it appears that the resulting lignin was also more reactive when the volatiles had been drawn off and condensed, just prior to a flash blowdown, or atmospheric decompression.

EXAMPLE 3

Third Aspect: Addition of Mineral Acid Catalyst

A series of experiments were carried out soaking poplar chips in a sulphuric acid bath for a period of about two days. The acid absorbed was measured by titration with NaOH and varied between 0.05% and 0.64% of the dry weight of wood.

The acidified chips were processed using the steam explosion process in a manner exactly equivalent to that outlined in Example 1. FIG. 4 shows a plot of theoretical maximum glucose yield and actual glucose yield measured against a function of acid concentration. Note the nearly three-fold increase in yields at high concentrations. The acid catalyst was also found to shorten optimal cooking times, and reduce pentose losses, according to the approximate relationships taught hereinbefore at Equations (4) and (5), with Equation (4) being a very close fit to the data, and Equation (5) representing a range of acceptable variation. Note that the denominator of Equations (4) and (5) may be stated as $(1+[R]AC).^5$, with the constant R chosen between 2 and 80, for a progressively closer fit to the data points. Said acid addition step may also conveniently be accomplished introducing a gaseous atmosphere of sulfur dioxide, for example, prior, or with the steam introduction step, to induce the desired acid production directly by reaction with the water content of the feedstock.

Having now disclosed preferred embodiments of my invention, it is to be understood that the invention is to be defined solely by the scope of the appended claims.

I claim:

1. An improved method for increasing the accessibility of cellulose in lignocellulosic materials, such as hardwoods, bagasse and the like, to rumen bacteria, enzymes, microorganisms and the like, characterized by an optimization of a range of cooking times ($t_c$) which will respond to the actual pressure conditions in the reactor as they may change over time during a given cooking run and render the cellulose most open for attack by said microorganisms or enzymes, as measured by the rate or extent of their reaction, said method comprising the steps of:

(a) feeding lignocellulosic material, in a divided form, into a pressure reactor vessel; and (b) introducing pressurized steam into the vessel during a pressurization time phase so as to reach reactor pressures of between 250 and 1000 psig wherein said reactor pressures does follow a given time profile; and (c) cooking by maintaining the lignocellulosic material at said time variable pressures between 250 and 1000 psig for a total period of time ($t_c$) in seconds, which includes the pressurization phase, wherein $t_3 \leq t_c \leq t_4$ and the given reactor pressure time profile is used to determine $t_3$ and $t_4$ for that given cook run since $t_3$ is defined implicitly by $$\int_o^{t_3} 2\left(\frac{T_s - 250}{10}\right) dt = 58$$

and $t_4$ and defined implicitly by $$\int_o^{t_4} 2\left(\frac{T_s - 250}{10}\right) dt = 115$$

wherein $T_s$ is the temperature (°C.) of saturated steam, at the indicated reactor pressures and corresponds to the saturated steam temperature values along the indicated reactor pressure time profile, thereby also making $T_s$ a given function of time (t); and (d) decompressing the cooked lignocellulosic material down to substantially atmospheric pressure at the end of said cooking time, $t_c$.

2. A method as in claim 1, whereby said value of of $t_c$ is further within the range $t_3 < t_c < t_4$ wherein $t_c$ is defined implicitly and substantially by $$\int_0^{t_c} 2^{\left(\frac{T_s - 250}{10}\right)} dt = 81.$$

3. A method as in claims 1 or 2, wherein $T_s$ is maintained at a constant value, by the step of introducing said steam so as to achieve a given pressure, within approximately 15 seconds after the introduction of steam into the vessel, and maintaining said given pressure value constant in time until $t_c$ is reached.

4. A method as in claims 1 or 2, wherein a substantial amount of an inert gas under pressure also is introduced into the reactor and $T_s$ then is derived from the values of the indicated reactor pressure time profile reduced by the partial pressure of the additional inert gas.

5. A method as in claims 1 or 2, wherein the lignocellulosic feedstock comprises deciduous wood divided into chips approximately one inch long by approximately $\frac{1}{8}$ inch thick, and said reactor is loosely packed with said chips.

6. A method as in claims 1 or 2, wherein during the cooking step the reactor pressure time profile reaches pressures between 500 and 1000 psig.

7. A method as in claims 1 or 2, wherein during the cooking step the reactor pressure time profile reaches pressures between 500 and 750 psig.

8. A method as in claims 1 or 2, wherein said decompressing step is accomplished suddenly, within 10 seconds about $t_c$.

9. An improved method for increasing the accessibility of cellulose in lignocellulosic materials, such as hardwoods, bagasse and the like, to rumen bacteria, enzymes, microorganisms and the like, while reducing pentose sugar losses, characterized by an optimization of a range of cooking times ($t_c$) which will respond to the actual pressure conditions in the reactor as they may change over time during a given cooking run and render the cellulose most open for attack by said microorganisms or enzymes, as measured by the rate or extent of their reaction, said method comprising the steps of:
(a) feeding lignocellulosic material in a divided form into a pressure reactor vessel; and
(b) introducing pressurized steam into the vessel during a pressurization time phase so as to reach reactor pressures of between 250 and 1000 psig wherein said reactor pressures does follow a given time profile; and
(c) cooking by maintaining the lignocellulosic material at said time variable pressures between 250 and 1000 psig for a total period of time ($t_c$) in seconds, which includes the pressurization and purging phase, wherein $t_3 \leq t_c \leq t_4$ and the given reactor pressure time profile is used to determine $t_3$ and $t_4$ for that given cook run since $t_3$ is defined implicitly by:

$$\int_0^{t_3} 2^{\left(\frac{T_s - 250}{10}\right)} dt = 58$$

and $t_4$ is defined implicitly by:

$$\int_0^{t_4} 2^{\left(\frac{T_s - 250}{10}\right)} dt = 115$$

and wherein $T_s$ is the temperature (°C.) of saturated steam, at the indicated reactor pressures and corresponds to the saturated steam values along the indicated reactor pressure time profile, thereby also making $T_s$ a given function of time; and
(d) removing volatile degradation products from the pressure reactor vessel by purging gases from the reactor so as to reduce the pressure by at least 100 psig; and then
(e) suddenly decompressing the cooked lignocellulosic material by ejection through an outlet portion of the pressure reactor vessel in an explosive manner.

10. A method as in claim 9, wherein the total cooking time ($t_c$), including the pressurization and purging phases, is within the range $t_3 < t_c < t_4$ wherein $t_c$ is defined implicitly by $$\int_0^{t_c} 2^{\left(\frac{T_s - 250}{10}\right)} dt = 81.$$

11. A method as in claim 10, wherein a substantial amount of an inert gas under pressure also is introduced into the reactor and $T_s$ then is derived from the values of the indicated reactor pressure time profile reduced by the partial pressure of the additional inert gas.

12. A method as in claim 10, wherein $T_s$ is maintained at a constant value, by the step of introducing said stream so as to achieve a given pressure, within approximately 15 seconds after the introduction of steam into the vessel, and maintaining said given pressure value constant in time until $t_c$ is reached.

13. A method as in claim 10, wherein during the cooking step the reactor pressure time profile reaches pressures between 500 and 1000 psig.

14. A method as in claim 10, wherein during the cooking step the reactor pressure time profile reaches pressures between 500 and 750 psig.

15. A method as in claim 10, wherein said purging of volatile degradation products is accomplished within approximately 5 to 25 seconds.

16. A method as in claim 10, wherein the volatile degradation products removed by said purging step are condensed and recovered.

17. A method as in claim 1 or 9, which comprises the further step of neutralizing the pH of the decompressed, cooked lignocellulosic material with a suitable base.

18. An improved method for increasing the accessibility of cellulose in lignocellulosic materials, such as hardwoods, bagasse and the like, to rumen bacteria, enzymes, microorganisms and the like, while reducing pentose sugar losses, characterized by an optimization of a range of cooking times ($t_c$) which will respond to the actual pressure conditions in the reactor as they may change over time during a given cooking run and render the cellulose most open for attack by said microorganisms or enzymes, as measured by the rate or extent of their reaction, said method comprising the steps of:
(a) feeding a lignocellulosic feedstock material in a loose, divided form, which contains an added acid level that is equivalent to between 0.01 and 1% by weight of sulphuric acid, into a pressure reactor vessel; and (b) introducing pressurized steam into the vessel during a pressurization time phase so as to reach reactor pressures of between 250 and 1000 psig wherein said reactor pressures does follow a given time profile; and (c) cooking by maintaining the lignocellulosic material at said time variable pressures between 250 and 1000 psig for a total period of time ($t_c$) in seconds, including the pressurization phase, which is chosen so that $t_1 \leq t_c \leq t_2$ and the given reactor pressure time profile is used to determine $t_2$ for that given cook run since $t_2$ is defined implicitly by $$\int_0^{t_1} (1 + [R]AC)^{.5} 2\left(\frac{T_s - 250}{10}\right) dt = 135$$

and $t_1$ is defined implicitly by $$\int_0^{t_1} (1 + [R]AC)^{.5} 2\left(\frac{T_s - 250}{10}\right) dt = 43$$

where R is a constant that is chosen between 2 and 80, and where $T_s$ is the temperature (°C.) of saturated steam at the indicated reactor pressures and corresponds to the saturated steam temperature values along the indicated reactor pressure time profile, thereby also making $T_s$ a given function of time (t), and AC represents the added acid concentration to the lignocellulosic feedstock stated as an equivalent acid concentration in percent by weight of sulphuric acid; and (d) decompressing the cooked lignocellulosic material down to substantially atmospheric pressure, at the end of said cooking time, $t_c$.

19. An improved method for increasing the accessibility of cellulose in lignocellulosic materials, such as hardwoods, bagasse and the like, to rumen bacteria, enzymes, microorganisms and the like, while reducing pentose sugar losses, characterized by an optimization of a range of cooking times ($t_c$) which will respond to the actual pressure conditions in the reactor as they may change over time during a given cooking run and render the cellulose most open for attack by said microorganisms or enzymes, as measured by the rate or extent of their reaction, said method comprising the steps of:

(a) feeding a lignocellulosic feedstock into a reactor vessel, wherein said material is in a loose, divided form and contains no added acid level that is equivalent to between 0.01 and 1% by weight of sulfuric acid; and (b) rapidly introducing pressurized steam into the vessel during a pressurization time phase so as to reach reactor pressure between 250 and 1000 psig wherein said reactor pressures does follow a given time profile; and (c) cooking by maintaining the lignocellulosic material at said time variable pressures between 250 and 1000 psig for a total period of time ($t_c$) in seconds; and (d) removing volatile degradation products from the pressure reactor vessel by purging gases from the reactor so as to reduce the pressure by at least 100 psig, wherein the total cooking time ($t_c$), including the pressurization cooking and purging, is chosen so that $t_1 \leq t_c \leq t_2$ and the given reactor pressure time profile is used to determined $t_2$ for that given cook run since $t_2$ is defined implicitly by $$\int_0^{t_2} (1 + [R]AC)^{.5} 2\left(\frac{T_s - 250}{10}\right) dt = 135$$

and $t_1$ is defined implicitly by $$\int_0^{t_1} (1 + [R]AC)^{.5} 2\left(\frac{T_s - 250}{10}\right) dt = 43$$

wherein R is a constant that is chosen to have a value between 2 and 80, $T_s$ is the temperature (°C.) of saturated steam temperature values along the indicated reactor pressure time profile, thereby also making $T_s$ a given function of time (t), and AC represents the added acid concentration to the lignocellulosic feedstock stated as an equivalent acid concentration in percent by weight of sulphuric acid; and (e) suddenly decompressing the cooked lignocellulosic material substantially to atmospheric pressure by ejection through an outlet portion of the pressure reactor vessel in an explosive manner.

20. A method as in claim 18 or 19, wherein a substantial amount of an inert gas under pressure also is introduced into the reactor and $T_s$ then is derived from the values of the indicated reactor pressure time profile reduced by the partial pressure of the additional inert gas.

21. A method as in claim 18 or 19, wherein R is chosen to be 80.

22. A method as in claim 18 or 19, wherein $T_c$ is chosen so that $t_1 \leq t_c \leq t_2$, and $t_1$ is defined implicitly by $$\int_0^{t_1} (1 + [R]AC)^{.5} 2\left(\frac{T_s - 250}{10}\right) dt = 43$$

23. A method as in claim 22, wherein $T_s$ is maintained at a constant value, by the step of introducing said steam so as to achieve a given pressure, within approximately 15 seconds after the introduction of steam into the vessel, and maintaining said given pressure value constant in time until $t_c$ is reached.

24. A method as in claim 22, wherein during the cooking step the reactor pressure time profile reaches pressures between 500 and 1000 psig.

25. A method as in claim 22, wherein during the cooking step the reactor pressure time profile reaches pressures between 500 and 750 psig.

26. A method as in claim 22, which further comprises the additional step of neutralizing the pH of the decompressed, cooked lignocellulosic material with a suitable base.

27. A method as in claim 18 or 19, wherein the acid is a mineral acid.

28. A method as in claim 18 or 19, wherein the acid concentration is in an amount of 0.15 to 1% by weight.

29. A method as in claim 18 or 19, wherein the acid concentration is in an amount of 0.3 to 1% by weight.

30. A method as in claim 18 or 19, wherein said step of adding acid further comprises subjecting said feedstock to a gaseous atmosphere which is operable to react with a water content of said feedstock material to thereby form said acid concentration.

31. A method as in claims 18 or 19, further comprising the additional step of neutralizing the decompressed, cooked lignocellulosic material with a suitable alkali to a pH suitable for a subsequent alcohol production.

32. A method as in claim 1, 18 or 19, further comprising the additional step of neutralizing the pH of the decompressed, cooked lignocellulosic material with ammonia to a pH of approximately 7, thereby increasing the digestibility, by ruminants, of cellulose from said lignocellulosic material.

33. An improved control method for increasing the accessibility of cellulose in lignocellulosic materials, such as hardwoods, bagasse and the like, to rumen bacteria, enzymes, microorganisms and the like, while reducing pentose sugar losses, characterized by optimizing the cooking times ($t_c$) in response to the actual pressure conditions in the reactor as they may change over time during a given cooking run, in order to render the cellulose most open for attack by said microorganisms or enzymes, as measured by the rate or extent of their reaction, said control method comprising the steps of:
   (a) feeding a lignocellulosic feedstock material in a loose, divided form, which may also contain an acid level that is equivalent to less than 1% by weight of sulphuric acid, into a pressure reactor vessel; and
   (b) introducing pressurized steam into the vessel during a pressurization time phase so as to reach reactor pressures of between 250 and 1000 psig and monitoring in time said reactor pressures as it follows a given time profile; and
   (c) cooking by maintaining the lignocellulosic material at said time variable pressures between 250 and 1000 psig for a total period of time ($t_c$) in seconds, including the pressurization phase, which is chosen so that $t_c$ substantially is determined by the reactor pressure time profile so monitored, wherein the given reactor pressure optimum cook time profile is used to determine $t_c$ by integrating the pressure time profile over time until there is a substantial satisfaction of the mathematical relationship, as follows:

$$\int_o^{t_c} (1 + [R]AC)^{.5} \, 2^{\left(\frac{T_s - 250}{10}\right)} \, dt = 81$$

wherein R is a constant that is chosen as approximately 80, and wherein $T_s$ is the temperature (°C.) of saturated steam at the monitored reactor pressures and corresponds to the saturated steam temperature values along each point of the monitored reactor pressure time profile, thereby also making $T_s$ a given function of time (t), and wherein AC represents any added acid concentration to the lignocellulosic feedstock stated as an equivalent acid concentration in percent by weight of sulphuric acid; and
   (d) decompressing the cooked lignocellulosic material down to substantially atmospheric pressure, at the end of said cooking time, $t_c$.

34. A method as in claim 33, wherein said cooking step further comprises removing volatile degradation products from the pressure reactor vessel by purging gases from the reactor so as to reduce the pressure by at least 100 psig, wherein the total cooking time ($t_c$), includes the pressurization, cooking and purging steps.

35. A method as in claim 34, wherein $T_s$ is maintained at substantially at a constant value, by the step of introducing said steam so as to achieve given pressure within approximately 15 seconds after the introduction of steam into the vessel, and maintaining said given pressure substantially constant in time until $t_c$ is reached.

36. An improved method for increasing the level of accessibility of cellulose in lignocellulosic material such as hardwoods, bagasse and the like, said method comprising the steps of:
   (a) feeding lignocellulosic material in a divided form into a pressure reactor vessel; and
   (b) rapidly introducing pressurized steam into the vessel so as to reach a reactor pressure of between 250 and 1000 psig;
   (c) Cooking by maintaining the lignocellulosic material at a pressure of between 250 and 1000 psig for a period of time $t_c$ in seconds defined by the formula $$t_c = 81 \times 2^{\left(\frac{250 - T_s}{10}\right)}$$

wherein
   $T_s$ is the temperature (°C.) of saturated steam of said reactor pressure; and
   (d) suddenly decompressing the cooked lignocellulosic material down to substantially atmospheric pressure at the end of said cooking time, $t_c$.

37. An improved method for increasing the level of accessibility of cellulose in lignocellulosic material such as hardwoods, bagasse and the like, said method comprising the steps of:
   (a) feeding lignocellulosic material in a loose divided form, which contains an added acid level equivalent to between 0.01 and 1% by weight of sulphuric acid, into a pressure reactor vessel so as to reach a pH of 4 or lower; and
   (b) rapidly introducing pressurized steam into the vessel so as to reach a reactor pressure of between 250 and 1000 psig; and
   (c) cooking by maintaining the lignocellulosic material at a pressure of between 250 and 1000 psig for a period of time $t_c$ in seconds defined by the formula $$t_c = 81 \times (1.05 - \sqrt{AC}) \times 2^{\left(\frac{250 - T_s}{10}\right)}$$

wherein
   $T_s$ is the temperature (°C.) of saturated steam at the reactor pressure, and
   AC represents the added acid concentration to the lignocellulosic material stated as an equivalent acid concentration inppercent by weight of sulphuric acid; and
   (d) suddenly decompressing the cooked lignocellulosic material down to substantially atmospheric pressure at the end of the said cooking, $t_c$.

38. A method as in claims 36 or 37, wherein said cooking step further comprises removing volatile degradation products from the pressure reactor vessel by rapidly purging gasses from the reactor so as to reduce the reactor cooking pressure by at least 100 psig, wherein the total cooking time ($t_c$), includes the pressurization, cooking and purging steps.

* * * * *